United States Patent [19]

Provonchee

[11] Patent Number: 4,717,667
[45] Date of Patent: Jan. 5, 1988

[54] COLONY REPLICATING DEVICE

[75] Inventor: Richard B. Provonchee, Camden, Me.

[73] Assignee: FMC Corporation, Philadelphia, Pa.

[21] Appl. No.: 629,653

[22] Filed: Jul. 11, 1984

[51] Int. Cl.$^4$ .............................. C12M 1/26; C12Q 1/24
[52] U.S. Cl. .......................................... 435/292; 435/30
[58] Field of Search ................. 435/30, 287, 292, 293, 435/294, 297, 298, 299, 300, 301, 805; 128/759; 604/358, 385 R, 385 A, 386; 428/316.6

[56] References Cited

U.S. PATENT DOCUMENTS

| | | | |
|---|---|---|---|
| 3,512,518 | 5/1970 | Mishkin et al. | 128/2 |
| 3,684,660 | 8/1972 | Kereluk et al. | |
| 3,751,341 | 8/1973 | Seitz et al. | |
| 3,843,452 | 10/1974 | Freake et al. | 435/294 |
| 3,932,220 | 1/1976 | Liotta | 435/301 X |
| 3,935,099 | 1/1976 | Weaver et al. | 524/734 X |
| 3,996,934 | 12/1976 | Zaffaroni | 128/268 |
| 4,237,223 | 12/1980 | Metz | 435/30 |
| 4,250,256 | 2/1981 | Wielinger et al. | 435/34 X |
| 4,312,834 | 1/1982 | Vogel | 435/805 X |
| 4,368,272 | 1/1983 | Kashket | 435/293 |
| 4,397,955 | 8/1983 | Entis et al. | 435/293 X |
| 4,485,171 | 11/1984 | Ikeda et al. | 435/30 |
| 4,565,783 | 1/1986 | Hansen et al. | 435/299 |
| 4,591,567 | 5/1986 | Britten et al. | 435/293 |
| 4,634,676 | 1/1987 | Sapatino | 435/299 X |
| 4,659,672 | 4/1987 | Provonchee et al. | 435/299 X |

FOREIGN PATENT DOCUMENTS

| | | |
|---|---|---|
| 0085839 | 8/1983 | European Pat. Off. |
| 2927141 | 1/1981 | Fed. Rep. of Germany ...... 435/292 |

*Primary Examiner*—Robert J. Warden
*Assistant Examiner*—Randall E. Deck
*Attorney, Agent, or Firm*—Christopher Egolf; Eugene G. Horsky

[57] ABSTRACT

A device for replicating moist bacterial or other cell colonies including a rigid layer, a resilient backing layer secured to one side of the rigid layer and a cell colony transfer surface made from an open-cell, flexible foam which includes a hydrophilic material therein and which surface is absorbent, porous, compliant and exhibits less resilience than said backing layer.

14 Claims, 5 Drawing Figures

COLONY REPLICATING DEVICE

This invention relates to an improved device for replicating or transferring microbial or other cell colonies or aggregates from one culture growth medium to another, and particularly to a device which may be used to efficiently and faithfully transfer colonies from a first growth medium to a multiplicity of other media, which may be of the same or different composition.

In microbiological and other cell culture work it is common practice to nurture cell colonies on growth media, such as agar, contained in petri plates or dishes and to transfer such cell colonies to other like or different growth media or membranes to facilitate various tests, as for example, to determine colony response to chemical, pharmaceutical or biological agents. This colony transfer procedure is known as replica plating and, while it can be achieved by transferring one colony at a time by means of a single inoculating needle, this procedure is laborious. Moreover, as it is important that the spatial integrity of colonies be maintained, it is apparent that the single needle transfer procedure is much too dependent upon the skill and care of the technician.

The deficiencies of the single needle transfer procedure have, to some degree, been remedied by the use of a velvet pad which was proposed well over thirty years ago by Joshua and Ester Lederberg at the University of Wisconsin and still remains the most widely used system. This system simply involves snugly wrapping a velvet fabric over the end of a cylindrical wood or cork support, with the velvet nap or pile projecting outwardly, and retaining the fabric in place by a metal flange or hoop. After being sterilized, the velvet pile is contacted with the parent colonies under light pressure so as to pick-up the same. The colonies are then transferred by contacting the pile carrier with other growth media or membranes.

Whil the use of a velvet pad as described above does maintain the spatial integrity of the cell colonies, and is certainly more convenient than the use of a single inoculating needle, the conventional velvet pad itself has certain limitations. More specifically, a velvet pad is essentially a series of needle tips in a fixed array, with the space between such needle tips serving as a collector of moisture which the pad takes on when contacted with a growth medium and colony to be transferred. It is necessary that such moisture be accommodated, otherwise lateral smearing of replicates results. Obviously, the more moisture on the growth medium and/or colony surface, the more moisture accumulated within the pile of the velvet pad when it is contacted therewith, and the less efficient is such conventional velvet pad when replication is attempted. A velvet pad with a deep pile would, of course, provide more space within which moisture might collect, but would also have longer and more flexible projecting fibers or needle tips and thus form fewer and less faithful replicates.

The deficiencies of the conventional velvet pad and other similar replicating means have been overcome by a replicating device as described in U.S. patent application Ser. No. 345,966 now U.S. Pat. No. 4,659,672 filed jointly by R. B. Provonchee and D. W. Renn on Feb. 5, 1982, which includes a layer of hydrocolloid material formed on a stiff but flexible film and having an exposed surface which, when contacted with a cell colony absorbs moisture therefrom and into such layer and thereby picks up the colony on its surface. In the use of that device, as described in the cited application, it is necessary to flex the supporting film and layer of hydrocolloid material so that the exposed surface assumes a convex contour during its application to and removal from the parent colonies, and also during replication, so as to avoid the entrapment of air, and subsequently, the creation of a vacuum, between the growth medium and the surface of the hydrocolloid layer during its application and removal.

While the colony replicating device in said application Ser. No. 345,966 is satisfactory, and is certainly a welcome and long overdue advance over the use of a conventional velvet pad, users prefer still greater ease of use and assurance of consistently accurate replicates. Accordingly, a primary objective of this invention is an improved colony replicating device which is simple in construction and use and facilitates the formation of more faithful colony replicates.

Another object of this invention is a colony replicating device which requires a minimum of manipulation during use and is capable of absorbing excess moisture from growth media and/or cell colonies, and thus at least minimize colony displacement.

Still another object of this invention is a colony replicating device which is capable of providing a large number of replicates of high resolution.

These and other objects of the invention are achieved by a bacterial or other cell colony replicating device which comprises a resilient backing layer having on one side thereof a cell colony transfer surface which is absorbent, but of less resilience than said backing layer, and porous.

The resilient backing layer is one of the essential elements of the device of the present invention. Its simple construction is deceptive of the efficiencies that it imparts to the device of the present invention and, as evidenced by conventional replicating devices, its incorporation into the device here described is actually contrary to prevalent views as to the manner by which a replicating device performs its intended function. Not having recognized the cause of the deficiencies of conventional cell colony replicating devices, remedy of the problem has heretofore eluded those skilled in the art and is here clearly described and claimed.

More specifically, in departing from the use of a simple inoculating needle, conventional replicating devices were constructed so as to facilitate the application of the colony pick-up means thereof onto a host growth medium under a firm and essentially uniform pressure. While surface nonuniformity of a host growth medium is certainly apparent, conventional replicating devices illustrate well a lack of recognition that such differences along the surface of the host growth medium must be accommodated. Some such accomodation may well occur with these conventional devices by distortion of the cell colony pick-up means, and accompanying sacrifice in the resolution of the replicates as well as the durability or usefulness of the cell colony pick-up means itself. More likely, the surface contour of the host growth medium is distorted under the firm and essentially uniform pressure applied thereto by the device. Thus, it would appear that known colony transfer devices in fact provide for replicates of a distorted array of colonies from a host growth medium, and that even such replicates lack faithfulness and are relatively few in number.

The absorbency of the cell colony transfer surface is a prime consideration forr, as heretofore mentioned in connection with the conventional velvet pad system, moisture present in a growth medium may cause spreading of the cell colonies when replication is attempted. Moreover, it is not only the surface moisture that causes concern, it is also that moisture which is released from such medium when the transfer surface is urged into contact with the colonies under pressures necessary for pick-up and transfer of the cell colonies.

Also of importance is that the cell colony transfer surface be porous for it is this porosity that at least minimizes the entrapment of air and vacuum creation as the transfer surface is moved, respectively, toward and away from a cell colony growth medium during cell colony pick-up, and also during the formation of successive replicates thereof. Thus, not only is there ease of use, the risk of cell colony distortion is certainly minimized.

Upon contact of the cell colony transfer surface of the device of the present invention with a host growth medium under pressure applied to the side of the resilient backing layer opposite to the transfer surface, the backing layer, being more resilient than the cell colony transfer surface, deforms preferentially at least generally in response to the surface contour of the host growth medium. The cell colony transfer surface picks-up cell colonies and concomitantly absorbs excess moisture from the host growth medium and the cell colonies thereof. As heretofore mentioned, the porosity of the cell colony transfer surface serves to at least minimize the entrapment of air and the creation of a vacuum, respectively, during movement of the cell colony transfer surface into contact with and away from the host growth medium and, also, during the subsequent formation of successive replicates of the cell colonies thereon.

In the preferred construction of the device of this invention, as hereafter described in detail, the resilient backing member is porous. Rigid means, which may simply be a flat stiff plate or disk, is included for receiving and distributing pressure that is applied to the device. However, as distinguished from conventional replicating devices, the rigid means of the device of the invention is secured to the side of the resilient backing member opposite to the cell colony transfer surface. Thus, in lieu of pressure being transmitted directly to the cell colony transfer surface, as in conventioanl replicating devices, the rigid means receives and distributes the applied pressure to the resilient backing layer. In turn, and as described above, the resilient layer deforms in response to the surface contour of host growth medium and thereby provides at least some accommodation for irregularities along such medium surface.

The cell colony transfer surface is comprised of a hydrophilic material which is compliant so as to at least generally conform with the surface contour of the host growth medium under the pressure transmitted thereto by the resilient backing member. The greater the asorbency of the hydrophilic material, the more efficient is the cell colony transfer surface. A variety of hydrophilic materials will satisfy the requirements of absorbency, porosity, and compliancy which will provide a cell colony transfer surface that gives satisfactory, if not optimum results. Such hydrophilic materials include, for example, conventional cut-pile velvet, dense but porous paper, such as conventional filter or blotting papers, woven fabrics, nonwoven fabrics, such as a felt, particles of a diatomite, such as diatomaceous earth, nitrocellulose membranes, nylon filter membranes and natural hydrocolloids, for example, galactomannans, such as, locust bean gum, guar gum, and tara gum, calcium alginate, collagen, gelatin, carrageenan, including the kappa, iota, and lambda fractions, essentially alone or in any combination thereof, and agar and agarose and their hydroxyethyl derivatives. Fully synthetic water-insoluble or partially water-soluble hydrocolloids are also well adapted for use in the present invention and include materials, such as, polyacrylamide, polyvinyl alcohol, polyethylene glycol, and polyethylene oxides. Further, certain semi-synthetic derivatives of hydrocolloids are useful in the device of this invention, such as, starch and cellulose graft copolymers.

Some of the hydrophilic materials mentioned above will function better than others. For example, uncoated, fine-pored filter or blotting papers provide cell colony transfer surfaces which are compliant, absorbent, and porous and serve well when just a few cell colony replicates are desired as, when wet, and especially in the presence of excessive moisture, their structural stability suffers with repeated usage.

Particles of a diatomite, such as diatomaceous earth, carried by a layer of water-based latex binder also provide a highly satisfactory cell colony transfer surface. Such particles are inert and are capable of absorbing from 1.5–4.0 times their weight in water. They are preferably retained or embedded in a film of latex material, such as acrylic water-based emulsion copolymers, such as available under the trademark Rhoplex from Rohm & Haas Co. of Philadelphia, Pa. Such water-based latex binders do not inhibit the absorbent characteristics of the diatomaceous earth as they are, in themselves, hydrophilic, yet do not readily dissolve in the presence of water.

Of the hydrocolloid materials, preferred are the abosrbent compositions comprising water-insoluble alkali salts of a polyacrylate, such as, sodium polyacrylates, and water-insoluble alkali salts of gelatinized-starch-polyacrylonitrile graft copolymers containing gelatinized starch (GS) and saponified polyacrylonitrile (HPAN) in molar ratios of from about 1:1.5 to 1:9 GS:HPAN. These compositions are described and are prepared as set forth in U.S. Pat. No. 3,935,099, the teachings of which are incorporated herein. The absorbent compositions of U.S. Pat. No. 3,935,099 have been referred to in the literature as "super slurper," and rightly so, for they are characterized as water-insoluble solids capable of absorbing in excess of 300 parts of water, by weight, per part of the water-insoluble solids. These and similar polymers, which are referred to as superabsorbent polymers, have been made available commercially in various grades, which differ in absorbency, and under various trade names, as for example, "Water-lock" from Grain Processing Corp. of Muscatine, Iowa, "SGP Absorbent Polymer" from Henkel Corporation of Minneapolis, Minn., and STASORB TM from A. E. Staley Manufacturing Co. of Decatur, Ill.

The hydrocolloids mentioned are representative and can be used alone or in various combinations and may also be combined with nutrient or cell colony maintenance media, non-toxic surfactants, fillers, and/or humectants. Obviously the hydrocolloid selected must be inert, it being understood that the term "inert," as used herein in connection with the hydrocolloids, as well as other materials mentioned for use in the device of the present invention, means that such materials do not enter into chemical or biological reactions and thus neither affect nor are affected by the colonies or the environment of such colonies.

As the hydrocolloid absorbs moisture, there may be a tendency for the hydrocolloid to slough off the backing layer and end up on the growth media during replication. Thus, to avoid this effect, it is preferred that a binder be combined with the hydrocolloid. Any inert binders which are or can be rendered hydrophilic and do not rapidly dissolve in the presence of water are suitable. Satisfactory results have been achieved using latex materials, such as acrylic water-based emulsion copolymers heretofore mentioned, and particularly a high strength, high gel temperature agarose (HGI agarose), available as Sea Kem HGT Agarose from FMC Corporation, Rockland, Me.

The amounts of hydrocolloid and binder employed may well vary with factors, such as, the particular hydrocolloid and binder selected, the degree of absorption desired, and the number of replicas to be made, and desirably may range, by weight, from about 0.01 to 99% hydrocolloid and from about 0.01 to 30% binder, preferably from about 0.1 to 30% when a latex is used and from about 0.01 to about 20% when HGT agarose is employed as a binder.

The porosity of the cell colony transfer surface is of importance as it permits air to escape as the cell colony transfer surface is urged into contact with a growth medium and also allows the entry of air when such transfer surface is removed from a growth medium. Air entrapment and the creation of a vacuum between the cell colony transfer surface and growth medium are thus completely avoided and without the need to flex the device, as with the device described in the above referred to patent application, or to apply concentrated pressure to the center of the backing layer, as to insure lateral expulsion of air from between the transfer surface and growth medium. Thus, aside from the ease of use, with the device of the present invention the cell colony transfer surface is generally planar when applied to and released from the growth media, and thereby contributes to the formation of replicas which are consistent and of high resolution.

For reasons as heretofore described, it is essential that the backing layer be resilient and, also, that its resilience exceed that of the cell colony transfer surface so that it will deform preferentially in response to pressure applied to the device. While the resilient backing layer may be of any desired construction, desirably it is porous and, more preferably, of an open cell, flexible foam structure so that it is not only very resilient, but also assists the porous cell colony transfer surface in preventing the entrapment of air and/or the creation of a vacuum between such transfer surface and a growth medium, as heretofore explained. Open cell, flexible foam structures are commercially available and are made of plastics, such as, polypropylene, polyester, nylon, polyurethane, and the like. The backing layer may be formed of other materials, such as paper, woven, nonwoven, and cut-pile (velvet) fabrics formed of natural fibers or synthetic fibers and glass, plastic or metal fibers, and cellulosic or rubber foam. Care must be exercised in the selection of materials and in the construction of such backing layer to insure that it exhibits resiliency, and a resiliency which is greater than that of said cell colony transfer surface.

The hydrophilic material comprising the cell colony transfer surface, if in integral form, such as a cut-pile velvet or blotting paper, may be simply bonded to the resilient backing layer, as with a water-based latex binder.

On the other hand, a hydrocolloid composition, or a binder containing diatomaceous earth, may be applied to the backing layer preferably as a viscous fluid, using water or other suitable solvent or dispersing agent, in any convenient manner, such as, by troweling, spraying, rolling, immersion or casting. Some slight penetration of the hydrocolloid composition or binder into the backing layer will occur and when subsequently dried, as by radiant lamps, oven, or ambient atmosphere, may well contribute to reducing the resiliency of the cell colony transfer surface. Moreover, upon drying, and thus shrinking, the hydrocolloid composition or binder, the transfer surface will generally reflect the porosity of the adjacent portion of the resilient backing layer; that is, being continuous in the areas thereof that extend between pores. If necessary, backing layers formed of plastic materials may be subjected to a corona discharge or other treatment to render the same receptive; that is, adherent, to the hydrocolloid composition and/or binder.

In the event the applied hydrocolloid composition and/or binder does not possess the desired porosity, minute performations may be imparted by any conventional means, as by a pin-wheel perforator or laser beam.

As it is not uncommon to encouter for replication, colonies which are very small; that is, less than 1 mm, a backing layer having relatively large pore size may necessitate the incorporation of a filler or bulking agent into the hydrocolloid composition so as to partially fill or reduce such pore openings. For example, when using a fine cell reticulated or open cell polyurethane foam having 100 pores per linear inch, it was found very desirable to incorporate a filler within the hydrocolloid composition to effectively reduce the size of the pore openings, otherwise only portions of colonies were picked up by the transfer surface.

Any inert materials which can serve as fillers or bulking agents in the form of fine particles or powder may be employed, such as, particles of microcrystalline cellulose, agar, and talc, with particularly good results having been achieved by the use of diatomaceous earth. The filler particles must, of course, be a size smaller that the poor which are to be partially filled and will vary in amount according to the number and size of the pores in the backing layers.

The use of diatomaceous earth, in combination with a hydrocolloid material is highly desirable regardless of whether or not a filler is necessary, and is preferred. As heretofore described, the high water absorbing capacity of diatomaceous earth cooperates with the hydrocolloid material to provide a cell colony transfer layer having exceptionally high water take-up, retention, and distribution characteristics. As a result, cell colony replication can be performed rapidly and with a minimum of colony distortion, if any, even under adverse conditions encountered with excessively moist growth media and/or cell colonies.

Desirably, the transfer surface is pliable at the time of use and with close control of the water content of the hydrocolloid composition during application, drying, and packaging the need for a plasticizer may not exist. Yet, as such close control is not always possible or practiced, it is preferable to incorporate a plasticizer or humectant into the hydrocolloid composition, such as, glycerine, polyethylene glycol, propylene glycol, and the like. The amount of plasticizer employed in the composition may range, for example, from 0 to not more than 50% by weight.

In addition to the absorbency and porosity of the cell colony transfer surface, its pliability enables it to conform with irregularities in the surface of the growth medium with which it is contacted, and without the application of excessive pressure which may well cause colony spreading. The meniscus which is formed by the growth medium (agar) at the very edge of a petri plate is the most obvious of such irregularities. Together with the pliability of the transfer surface, its porosity cooperates to impart resilience to the transfer layer; that is, its ability to return to a generally planar condition after having been made to conform to the surface irregularities of a growth medium.

As heretofore discussed, the backing layer is more resilient than the cell colony transfer surface so that pressure applied to the device is not transmitted directly to the transfer surface but, instead, is absorbed in part and distributed generally along the entire area of the transfer surface. Thus, by avoiding the concentration of pressure on the transfer surface, spreading of the colonies on the growth medium is certainly minimized if not avoided.

This difference in resilience between the backing layer and cell colony transfer surface may well be achieved, for example, by the slight penetration of the diatomaceous earth and binder and/or hydrocolloid composition into the adjacent portion of the backing layer. More desirably, laminated onto backing layer is a lamina, formed of like or different materials and having a like or different internal structure, which is less resilient than the backing layer and which is a part of the cell colony transfer surface. For example, a thin layer of an open cell or reticulated, resilient polyurethane foam, having about 100 pores per lineal inch, laminated onto a similar but thicker layer of reticulated polyurethane foam having cells of larger size, and thus having less than 100 pores per inch and being more resilient, has served admirably in providing a cell colony transfer surface which is less resilient than the backing layer, yet is pliable and porous.

While generally understood in the art, mention is here made that the terms "reticulated" and "open cell" in connection with foam materials mean that foam has walls defining an internal cell structure of interconnecting cells; that is, the walls of normally closed foam cells have been ruptured or partially or completely removed, leaving an integral structure of webs or areas at which such closed foam cells were in contact.

In the drawing, FIG. 1 is a diagrammatic illustration of the device of the present invention;

Figure 1:
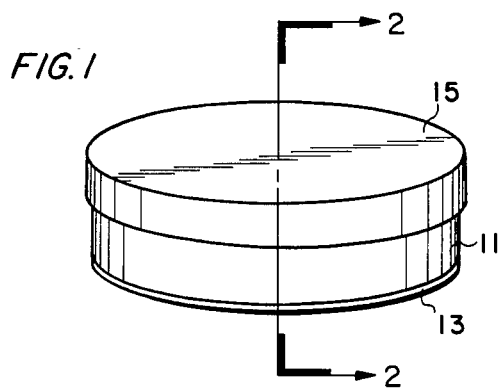
Figure 2:
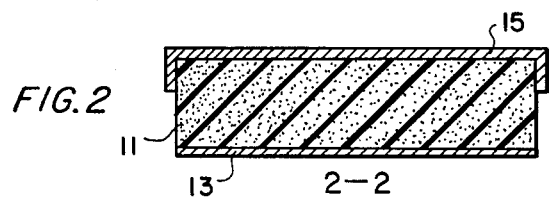
FIG. 2, is a vertical section taken along the line 2—2 of FIG. 1.

Referring to FIGS. 1 and 2 of the drawing, the device of the present invention includes a resilient backing layer 11, an absorbent and porous cell colony transfer surface 13, which is less resilient than the backing layer and which may consist of a layer of blotting paper or the like or other hydrophilic materials, such as, a diatomite embedded within a water-based latex material or a hydrocolloid. Adhesively fixed onto the resilient backing layer 11 is a rigid cap 15 by which pressure applied to the device is transmitted uniformly to the backing layer 11. The backing layer 11, as shown in FIG. 2, is formed of open cell foam material, although other materials having the necessary resiliency may be employed.

Figure 3:
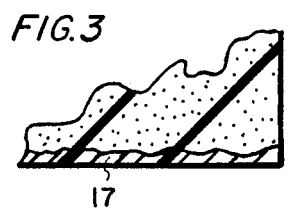
FIG. 3 is a fragmentary view, on an enlarged scale, of a portion of the device shown in FIG. 2.

Turning now to FIG. 3, the fragmentary view illustrates a portion of a resilient backing layer 11 comprised of a reticulated foam and a cell colony transfer surface comprised of a hydrocolloid, as for example, a water-insoluble alkali-salt of a polyacrylate, such a sodium polyacrylate, or of a gelatinized-starch-polyacrylonitrile graft copolymer, which penetrates slightly into the backing layer 11, as indicated at 17.

Figure 4:
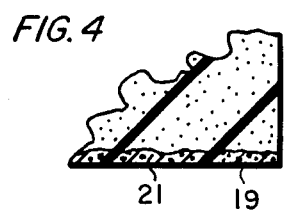
FIGS. 4 and 5 are view similar to that of FIG. 3 showing further embodiments of the device of this invention.

The modification shown in FIG. 4 differs from that shown in FIG. 3 primarily in that the cell colony transfer surface 13 comprised of a water-based latex binder 19 having particles 21 of a diatomite embedded therein.

Figure 5:
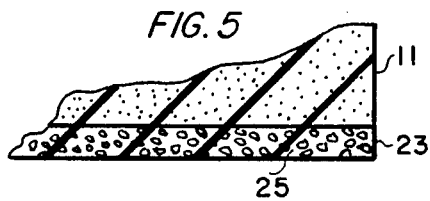

In the still further modification shown in FIG. 5, the device is comprised of a fine cell reticulated foam 23 adhesively bonded, as by a water-based latex binder, to the resilient backing layer 11 and includes a hydrocolloid 25, such as that shown in FIG. 3, contained within the open cells of such foam 23.

To still further illustrate the merits of the device of the present invention, reference is made to the following examples.

EXAMPLE I

Materials employed for preparing cell colony replicating devices of this invention were as follows:
(1) Water-Lock J-500 superabsorbent polymer—a water-insoluble sodium polyacrylate—available from Grain Processing Corp. of Muscatine, Iowa, and referred to herein as "super-absorbent polymer."
(2) HGT Agarose—High strength, high gel temperature agarose, available as Sea Kem HGT Agarose from FMC Corporation, Rockland, Me.
(3) Glycerine.
(4) Distilled, Deionized water.
(5) Foam discs—3 5/6" diameter×¼" thick open cell, polyurethane foam, about 100 pores per linear inch, available from Scott Paper Co.
(6) Petri dishes and lids, 100×25 mm.

24 ml of glycerine (3) was mixed with 900 ml of water (4) in a Waring blender with a Variac, variable power supply, used to adjust the blender speed to provide a vigorous vortexing of the mixture. 9.0 grams of the superabsorbent polymer (1) was then added, the blender speed was increased, and mixing was continued until shearing of the mixture ceased. With the blender stopped, the mixture was stirred with a spatula, after which the blender was operated at slow speed and the spatula was used to scrape the sides of the blender jar to insure that a smooth mixture of nongranular texture was obtained.

This mixture was then gently heated at 70°–80° C. during the addition of 3 grams of HGT agarose (2) dissolved in 300 ml of heated water and the mixture was stirred using a Talboy-type stirrer with a standard three-bladed paddle. This solution was then maintained at a temperature of 60°–70° C.

Using a spatula, approximately 8 ml of the solution was uniformly applied to each of a number of foam discs (5) and was pressed into the discs just below the exposed surfaces thereof.

The discs were placed in a hot-air oven at 60° C. for two hours. Equally effective results were obtained with overnight drying in a forced-air oven with no heat, and after 48 hours in the ambient atmosphere.

The resulting coated foam discs were then secured to the insides of petri dish lids by an adhesive applied to their surfaces opposite their coated sides, after which each such lid was sealed to a petri dish with a vinyl tape.

EXAMPLE II

The procedure and materials as described in Example I were employed with the addition 120 grams of diatomaceous earth was added and blended into the mixture prior to the addition of the dissolved HGT agarose. The diatomaceous earth was added primarily as a bulking agent to partially fill the pores of the side of the foam disc to which the solution was applied and thus provide a cell colony transfer surface with pores of reduced sized.

dishes. The replicates were incubated for 12 hours at 28° C. and then examined for five different factors and evaluated for ease of use. Assessed were (1) individual colony spreading, (2) streaking of colonies due to moisture accumulation, (3) individual colony "dropout" or loss, (4) whole plate pattern loss, and (5) presence or absence of satellite colonies. A detailed presentation of the results may be found in Table I.

By far the Device of Example I was the most efficient and easiest to use. However, it will be noted that all of the materials A through E did exhibit improvement in efficiency when incorporated into cell colony transfer devices in accordance wtih the present invention; that is, in the presence of a resilient backing layer and a rigid means (petri dish lid) for receiving and distributing to the resilient backing layer pressure applied to the respective devices.

TABLE I

|  | Unsupported | | | | | Film Supported | | | | | Pad Supported | | | | | Device of Example I |
|---|---|---|---|---|---|---|---|---|---|---|---|---|---|---|---|---|
|  | A | B | C | D | E | A | B | C | D | E | A | B | C | D | E |  |
| Individual Colony Spreading Under Pressure | 1 | 1 | 1 | 1 | 1 | 1 | 1 | 1 | 1 | 1 | 1 | 1 | 1 | 1 | 1 | 1 |
| Streaking (Moisture Accumulation) | 1 | 1 | 0 | 0 | 1 | 1 | 1 | 0 | 2 | 1 | 1 | 1 | 0 | 0 | 0 | 0 |
| Individual Colony Dropout | 1 | 1 | 2 | 1 | 1 | 1 | 1 | 1 | 2 | 1 | 2 | 1 | 1 | 0 | 3 | 0 |
| Whole Plate Pattern Loss | 2 | 1 | 4 | 2 | 1 | 3 | 3 | 2 | 5 | 3 | 0 | 0 | 1 | 0 | 5 | 0 |
| Satellite Colonies | + | + | + | + | + | + | + | − | − | − | + | + | − | − | − | − |
| Ease of Use | P | P | F | P | P | F | F | G | G | G | P | P | G | G | G | G |

The numbers above indicate the replicate which first exhibited the phenomenon referred to, and such phenomenon persisted, and in many instances became more pronounced, through all replicates thereafter. The symbol + indicates a presence, while the symbol − an absence of satellite colonies.
The letters G, F, and P designate "good," "fair," and "poor," respectively, while the letter O, indicates that a particular phenomenon referred to was not observed.

EXAMPLE III

In this Example an evaluation of the effectiveness was made of cell colony transfer surfaces as follows:
A. Nitrocellulose, available from Schleicher & Schuell, BA 85, 0.45 m.
B. Colony/Plaque Screen—microporous plastic, available from New England Nuclear Co.
C. Blotting paper—cellulose fiber—BRL DNA Blotter Pad.
D. Velvet—upholstery velvet, 2.5 mm nap.
E. Velveteen fabric—0.5 mm nap.

Each of the above materials was tested under the conditions, as follows:
1. Unsupported—the material was applied to the surface of the host plate, gently pressured to promote adhesion of the bacteria, and transferred to fresh plates in succession with forceps.
2. Film Supported—the material was fixed with rubber cement to the surface of a two-handled (tabs) disc of 0.2 mm polyester film. The resulting combination was applied in the same serial manner as the unsupported material.
3. Pad Supported—the material was mounted on a ¾" thick soft body of reticulated polyurethane foam pad in accordance with the present invention, which was then fixed to the lid of a 100 mm petri dish.

The above noted unsupported materials (1) and devices (2) and (3), and a cell colony replicating device, prepared as described in Example I, were evaluated by making eight replicates each from 8 hour old host plates of *E. coli* K12 JM105, with all replicates being made on Trypticase Soy Agar plates poured into 15×100 mm

I claim:
1. A device for replicating bacterial or other cell colonies comprising a layered structure of
   (i) a rigid layer means;
   (ii) a backing layer made of flexible foam which is secured to one side of the rigid means;
   (iii) a transfer layer which is attached to the side of the backing layer opposite from the rigid means and which is made from open-cell, porous, flexible foam; and
   (iv) a hydrophilic material included within the transfer layer and at its exposed surface, the hydrophilic material-containing foam transfer layer being air-porous and compliant but less resilient than the foam backing layer.
2. The device of claim 1 wherein the rigid means is a flat stiff plate.
3. The device of claim 1 wherein the flexible backing layer is open-cell, porous foam.
4. The device of claim 3 wherein the open-cell, porous foam of the backing layer is polyurethane.
5. The device of claim 3 wherein the open-cell, porous foam is a foam having less than 100 pores per inch.
6. The device of claim 1 wherein the transfer layer is laminated to the backing layer.
7. The device of claim 1 wherein the open-cell, porous foam of the transfer layer is polyurethane.
8. The device of claim 1 wherein the foam transfer layer is a foam having about 100 pores per inch.
9. The device of claim 1 wherein the hydrophilic material includes an additional component as a binder, plasticizer, filler, or bulking agent.

10. The device of claim 1 wherein the hydrophilic material includes diatomite particles.

11. The device of claim 1 wherein the hydrophilic material is a hydrocolloid.

12. The device of claim 11 wherein the hydrocolloid is selected from the group consisting of locust bean gum, guar gum, calcium alginate, collagen, gelatin, carrageenan, agar, agarose and hydroxyethyl derivatives thereof, water-insoluble alkali salts of polyacrylate, and water-insoluble alkali salts of gelatinized starch-polyacrylonitrile graft copolymers.

13. The device of claim 12 wherein the hydrocolloid is a water-absorbent water-insoluble alkali salt of gelatinized-starch polyacrylonitrile graft copolymer wherein the molar ratio of gelatinized starch to saponified polyacrylonitrile is from about 1:1.5 to 1:9.

14. The device of claim 13 wherein the gelatinized starch polyacrylonitrile graft copolymer is dispersed in a water-based latex binder.

* * * * *